United States Patent [19]

Karrer

[11] 4,172,146

[45] Oct. 23, 1979

[54] SUBSTITUTED PHENYL DERIVATIVES

[75] Inventor: Friedrich Karrer, Basel, Switzerland

[73] Assignee: Ciba-Geigy Corporation, Ardsley, N.Y.

[21] Appl. No.: 667,006

[22] Filed: Mar. 15, 1976

Related U.S. Application Data

[63] Continuation of Ser. No. 358,431, May 8, 1973, abandoned.

[51] Int. Cl.² .............................................. C07C 69/76
[52] U.S. Cl. .................... 424/308; 260/326.4; 260/465 E; 260/465 F; 260/465 G; 260/559 A; 260/559 D; 544/176; 560/36; 560/48; 542/426; 542/427; 542/429; 542/438; 542/440
[58] Field of Search ............... 260/473 G; 560/53, 52, 560/57, 61, 62; 424/308

[56] References Cited

FOREIGN PATENT DOCUMENTS 6607056 11/1966 Netherlands ..................... 260/473 G Primary Examiner—Paul J. Killos
Attorney, Agent, or Firm—Harry Falber; Frederick H. Rabin

[57] ABSTRACT

Compounds of the formula

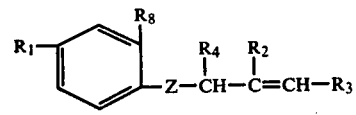
(I)

wherein $R_1$ represents cyclohexyl, cyclohexyloxy or the group

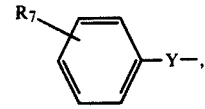

in which Y represents

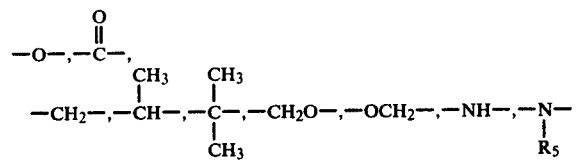

or the direct bond, Z represents

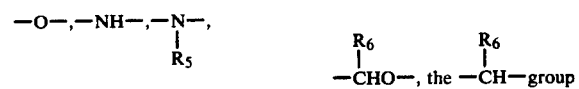

being bonded to the phenyl nucleus, $R_2$ represents hydrogen, $C_1-C_3$-alkyl, $R_3$ represents —COOH, ($C_1-C_5$-alkoxy)carbonyl, ($C_3-C_5$-alkenyloxy)carbonyl, ($C_3-C_5$-alkinyloxy)carbonyl, cyclohexyloxycarbonyl, phenoxycarbonyl, ($C_3-C_5$-haloalkenyloxy)carbonyl, the cyano group, a carbamoyl group which is mono- or disubstituted by $C_1-C_5$-alkyl, $C_3-C_5$-alkenyl or $C_3-C_5$-alkinyl, it being possible for the substituents of the carbamoyl group together with the nitrogen atom to which they are bonded to form a saturated 5- or 6-membered heterocyclic ring which can contain in addition an oxygen, a sulphur, or a further nitrogen atom, $R_4$ represents hydrogen, methyl, or ethyl, $R_5$ represents $C_1-C_3$-alkyl, formyl, or acetyl, $R_6$ represents hydrogen or $C_1-C_3$-alkyl, $R_7$ represents hydrogen, halogen, $C_1-C_5$-alkoxy or $C_1-C_5$-alkyl, and $R_8$ represents hydrogen, halogen, methyl, or ethyl, and their use in pest control are disclosed.

19 Claims, No Drawings

SUBSTITUTED PHENYL DERIVATIVES

This is a continuation of application Ser. No. 358,431 filed on May 8, 1973, now abandoned.

The invention relates to substituted phenyl derivatives, their manufacture, and their use in pest control.

The compounds correspond to the general formula

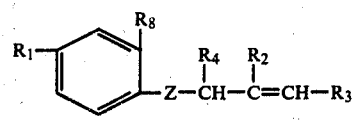

wherein $R_1$ represents cyclohexyl, cyclohexyloxy or the group

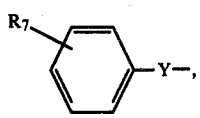

in which Y represents

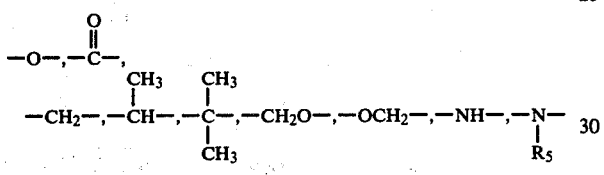

or the direct bond, Z represents

being bonded to the phenyl nucleus, $R_2$ represents hydrogen, $C_1$–$C_3$-alkyl, $R_3$ represents —COOH, ($C_1$–$C_5$-alkoxy)carbonyl, ($C_3$–$C_5$-alkenyloxy)carbonyl, ($C_3$–$C_5$-alkinyloxy)carbonyl, cyclohexyloxycarbonyl, phenoxycarbonyl, ($C_3$–$C_5$-haloalkenyloxy)carbonyl, the cyano group, a carbamoyl group which is mono- or disubstituted by $C_1$–$C_5$-alkyl, $C_3$–$C_5$-alkenyl or $C_3$–$C_5$-alkinyl, it being possible for the substituents of the carbamoyl group together with the nitrogen atom to which they are bonded to form a saturated 5- or 6-membered heterocyclic ring which can contain in addition an oxygen, a sulphur, or a further nitrogen atom, $R_4$ represents hydrogen, methyl, or ethyl, $R_5$ represents $C_1$–$C_3$-alkyl, formyl, or acetyl, $R_6$ represents hydrogen or $C_1$–$C_3$-alkyl, $R_7$ represents hydrogen, halogen, $C_1$–$C_5$-alkoxy or $C_1$–$C_5$-alkyl, and $R_8$ represents hydrogen, halogen, methyl, or ethyl.

Halogen is to be understood as meaning fluorine, chlorine, bromine, or iodine.

The alkyl or alkoxy groups represented by $R_5$, $R_6$, and $R_7$ can be straight-chain or branched. Examples of such groups include: methyl, ethyl, n-propyl, isopropyl, i-, n-, sec.- and tert.butyl, n-, sec.- and iso-pentyl, methoxy, ethoxy, propoxy, n-, iso- and sec.butoxy, n-pentoxy.

The alkoxy, alkenyloxy, alkinyloxy and haloalkenyloxy moieties of an alkoxycarbonyl, alkenyloxycarbonyl, alkinyloxycarbonyl or haloalkenyloxycarbonyl group $R_3$ can be straight-chain or branched. Examples of such moiety groups include: methoxy, ethoxy, n-propoxy, isopropoxy, sec.butoxy, allyloxy, methallyloxy, propargyloxy, chlorallyloxy. The alkyl, alkenyl or alkinyl substituents of a carbamoyl group $R_3$ can be straight-chain or branched. Examples of such a carbamoyl group $R_3$ include: monomethylcarbamoyl, monoethylcarbamoyl, dimethylcarbamoyl, diethylcarbamoyl, monoallylcarbamoyl, monoisopropylcarbamoyl, diallylcarbamoyl, 2-but-3-inyl-carbamoyl.

Examples of the heterocyclic rings formed with the substituents of the carbamoyl group $R_3$ together with the nitrogenatom to which they are bonded and optionally with a further heteroatom include the morpholine, piperidine, or pyrrolidine ring.

Compounds to be highlighted are those of the general formula I, wherein $R_1$ represents cyclohexyl, cyclohexyloxy, or the group

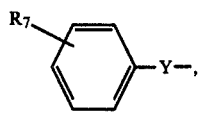

in which Y represents

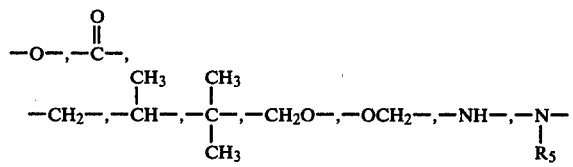

or the direct bond, Z represents —O—, —NH—,

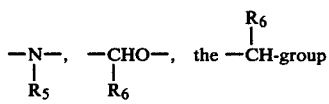

being bonded to the phenyl nucleus, $R_2$ represents hydrogen, methyl, or ethyl, $R_3$ represents carboxyl, methoxycarbonyl, ethoxycarbonyl, n-propoxycarbonyl, isopropoxycarbonyl, sec.butoxycarbonyl, cyclohexyloxycarbonyl, phenoxycarbonyl, allyloxycarbonyl, chlorallyloxycarbonyl, propargyloxycarbonyl, monomethylcarbamoyl, monoethylcarbamoyl, monoisopropylcarbamoyl, mono-sec. butylcarbamoyl, monoallylcarbamoyl, diethylcarbamoyl, diallylcarbamoyl, 2-but-3-inyl-carbamoyl, N-piperidinocarbonyl, n-morpholinocarbonyl or cyano, $R_4$ represents hydrogen or methyl, $R_5$ represents formyl or acetyl, $R_6$ represents hydrogen or methyl, $R_7$ represents hydrogen, $C_1$–$C_3$-alkyl, chlorine, methoxy or ethoxy, and $R_8$ represents hydrogen, chlorine or methyl.

Preferred compounds on account of their action are those of the general formula I, wherein $R_1$ represents the group

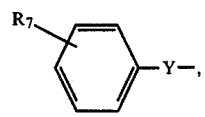

in which Y represents —O—,

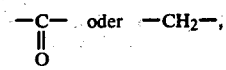

Z represents —O—, —CH₂O—, —NH—,

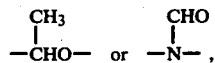

$R_2$ represents methyl or ethyl, $R_3$ represents methoxycarbonyl, ethoxycarbonyl, isopropoxycarbonyl, sec.-butoxycarbonyl, cyclohexyloxycarbonyl, monoethylcarbamoyl, diethylcarbamoyl, monoisopropylcarbamoyl, monoallylcarbamoyl, N-piperidinocarbonyl or cyano, $R_4$ represents hydrogen or methyl, and $R_7$ represents hydrogen, methyl, ethyl, chlorine, methoxy or ethoxy.

A particularly preferred group of compounds is that of the formula I, wherein $R_1$ represents the group

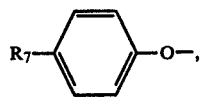

Z represents —O—, $R_2$ represents methyl or ethyl, $R_3$ represents methoxycarbonyl, ethoxycarbonyl, isopropoxycarbonyl, sec.butoxycarbonyl, diethylcarbamoyl, monoethylcarbamoyl or cyano, $R_4$ represents hydrogen, and $R_7$ represents hydrogen, chlorine, or ethyl.

A further preferred group of compounds is that of the formula I, wherein $R_1$ represents unsubstituted benzyl, Z represents —O—, $R_2$ represents methyl, $R_3$ represents methoxycarbonyl, ethoxycarbonyl, diethylcarbamoyl or cyano, and $R_4$ represents hydrogen.

The compounds of the formula I are manufactured in known manner, e.g. by the following methods:

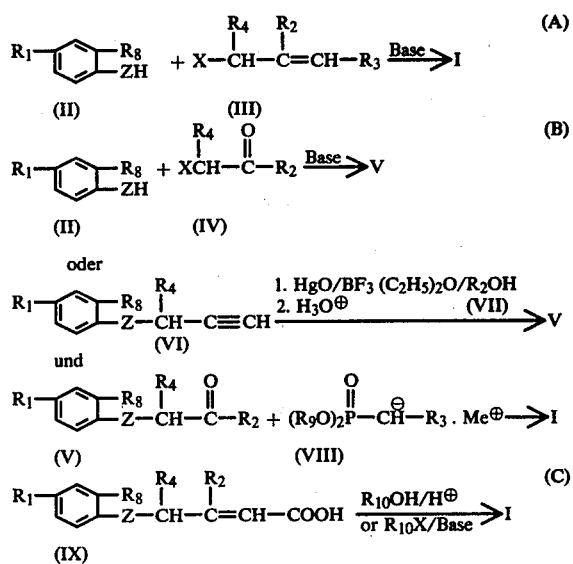

In the formula II to IX, Z and $R_1$ to $R_{10}$ have the meanings given for the formula I, X represents halogen, in particular chlorine or bromine, $R_9$ represents $C_1$-$C_5$-alkyl, phenyl or p-chlorophenyl, Me represents alkali metal, in particular sodium or potassium, and $R_{10}$ represents $C_1$-$C_4$-alkyl, $C_3$-$C_4$-alkenyl, $C_3$-$C_4$-alkinyl, or cyclohexyl.

Suitable bases in the reactions A, B and C are hydrides, amides, alkoxides, hydroxides, or carbonates of alkali or alkaline earth metals.

The starting materials of the formula IX are appropriately obtained by alkaline hydrolysis of a corresponding ester.

According to process B, the compounds of the formula I are manufactured by reacting a ketone of the formula IV with the anion of a dialkylphosphonic acid derivative in an inert solvent (Horner reaction, e.g. J. Org. Chem. 25, 1232–34 (1960) and J. Org. Chem. 30, 680 ff (1965)).

(D) The compounds of the formula I, wherein Y and/or Z represents the group

are appropriately manufactured by acylation or alkylation of a —NH group according to the following equations:

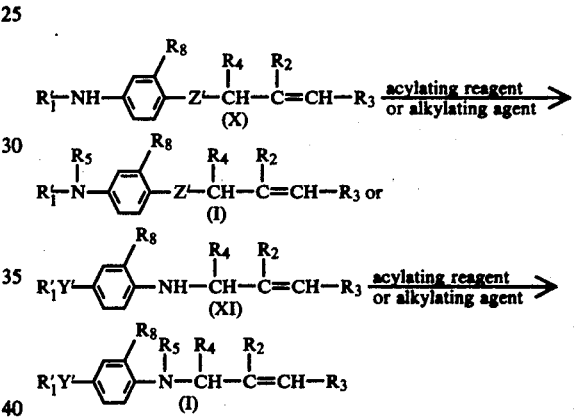

in which formulae $R_2$ to $R_8$ have the meanings given for formula I, $R'_1$ represents cyclohexyl or the group

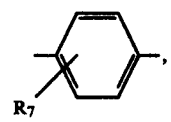

Z' represents —O—,

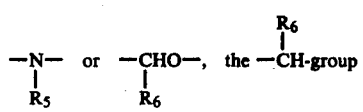

being bonded to the phenyl nucleus, and Y' represents

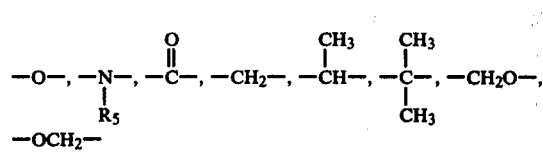

or the direct bond.

As acylating reagent there is used for example acetic acid-formic acid anhydride, acetic anhydride, or acetyl chloride in the presence of a base, such as a tertiary amine.

The reactions to the active substances of the formula I are carried out at normal pressure and in solvents and diluents which are inert towards the reactants, for example in aromatic hydrocarbons such as benzene, toluene, xylene; also in tetrahydrofuran, dioxan, dialkyl ethers; N,N-dialkylated amides, such as dimethyl formamide; in alcohols, such as methanol, ethanol, propanol, isopropanol, or butanols, sulphoxides, ketones, such as acetone, methyl ethyl ketone, or cyclohexanone. The reaction temperatures are in the range from 0°–140° C., but are preferably in the range from 10°–70° C.

The starting materials of the formulae II, III, IV, VI and VIII are known compounds. The compounds of the formula VII for example can be manufactured by the process disclosed in J. Org. Chem. 24, 434 (1959). During the manufacture of the compounds of the formula I by processes A, B and C, both possible geometrical isomers are formed in varying ratios.

The described componds partly constitute mixtures of these cis- and trans-isomers such as occur during the synthesis or after the purification.

Pure trans-isomers of the formula I can be obtained e.g. by the use of pure 3-alkyl-(or 3,4-dialkyl-)4-halogeno-2-trans-butenecarboxylic acid derivatives (J.A.C.S. 90 6225 [1968]) in the synthesis of the active substances, or by fractionated crystallisation, fractionated distillation, gas or adsorption chromatographic methods of separating cis/trans-isomer mixtures.

The compounds of the formula I can be used for combating animal and plant pests. In particular they are suitable for combating insects of the families:

Tettigonidae, Gryllidae, Gryllotalpidae, Blattidae, Reduviidae, Phyrrhocoridae, Cimicidae, Delphacidae, Aphididae, Diaspididae, Pseudococcidae, Scarabaeidae, Dermestidae, Coccinellidae, Tenebrionidae, Chrysomelidae, Bruchidae, Tineidae, Noctuidae, Lymatriidae, Pyrallidae, Culicidae, Tipulidae, Stomoxydae, Trypetidae, Muscidae, Calliphoridae and Pulicidae.

The insecticidal action can be substantially broadened and adapted to suitable the particular circumstances by the addition of other insecticides and/or acaricides as well as insect baits. Examples of suitable additives include the following known additives:

Organic Phosphorus Compounds

Bis-O,O-diethylphosphoric acid anhydride (TEPP)
Dimethyl-(2,2,2-trichloro-1-hydroxyethyl)-phosphonate (TRICHLORFON)
1,2-dibromo-2,2-dichloroethyldimethylphosphate (NALED)
2,2-dichlorovinyldimethylphosphate (DICHLORVOS)
2-methoxycarbamyl-1-methylvinyldimethylphosphate (MEVINPHOS)
Dimethyl-1-methyl-2-(methylcarbamoyl)-vinylphosphate cis (MONOCROTOPHOS)
3-(dimethoxyphosphinyloxy)-N,N-dimethyl-cis-crotonamide (DICROTOPHOS)
2-chloro-2-diethylcarbamoyl-1-methylvinyldimethylphosphate (PHOSPHAMIDON)
O,O-diethyl-O(or S)-2-(ethylthio)-ethylthiophosphate (DEMETON)
S-ethylthioethyl-O,O-dimethyl-dithiophosphate (THIOMETON)
O,O-diethyl-S-ethylmercaptomethyldithiophosphate (PHORATE)
O,O-diethyl-S-2-(ethylthio)ethyldithiophosphate (DISULFOTON)
O,O-dimethyl-S-2-(ethylsulphinyl)ethylthiophosphate (OXYDEMETON METHYL)
O,O-dimethyl-S-(1,2-dicarbethoxyethyldithiophosphate (MALATHION)
O,O,O,O-tetraethyl-S,S'-methylene-bis-dithiophosphate (ETHION)
O-ethyl-S,S-dipropyldithiophosphate
O,O-dimethyl-S-(N-methyl-N-formylcarbamoylmethyl)-dithiophosphate (FORMOTHION)
O,O-dimethyl-S-(N-methylcarbamoylmethyl)-dithiophosphate (DIMETHOATE)
O,O-dimethyl-O-p-nitrophenylthiophosphate (PARATHION-METHYL)
O,O-diethyl-O-p-nitrophenylthiophosphate (PARATHION)
O-ethyl-O-p-nitrophenylphenylthiophosphate (EPN)
O,O-dimethyl-O-(4-nitro-m-tolyl)-thiophosphate (FENITROTHION)
O,O-dimethyl-O-2,4,5-trichlorophenylthiophosphate (RONNEL)
O-ethyl-O-2,4,5-trichlorophenylethylthiophosphate (TRICHLORONATE)
O,O-dimethyl-O-2,5-dichloro-4-bromophenylthiophosphate (BROMOPHOS)
O,O-dimethyl-O-(2,5-dichloro-4-iodophenyl)-thiophosphate (JODOFENPHOS)
4-tert.butyl-2-chlorophenyl-N-methyl-O-methylamidophosphate (CRUFOMATE)
O,O-dimethyl-O-(3-methyl-4-methylmercaptophenyl)-thiophosphate (FENTHION)
Isopropylamino-O-ethyl-O-(4-methylmercapto-3-methylphenyl)phosphate
O,O-diethyl-O-p-(methylsulphinyl)phenyl-thiophosphate (FENSULFOTHION)
O-p-(dimethylsulphamido)-phenyl-O,O-dimethylthiophosphate (FAMPHUR)
O,O,O',O'-tetramethyl-O,O'-thiodi-p-phenylenethiophosphate
O-ethyl-S-phenyl-ethyldithiophosphate
O,O-dimethyl-O-(α-methylbenzyl-3-hydroxycrotonyl)-phosphate
2-chloro-1-(2,4-dichlorophenyl)vinyl-diethylphosphate (CHLORFENVINPHOS)
1-chloro-1-(2,4,5-trichlorophenyl)vinyl-dimethylphosphate
O-[2-chloro-1-(2,5-dichlorophenyl)]vinyl-O,O-diethyl-thiophosphate
Phenylglyoxylonitriloxime-O,O-diethylthiophosphate (PHOXIM)
O,O-diethyl-O-(3-chloro-4-methyl-2-oxo-2-H-1-benzopyran-7-yl)thiophosphate (COUMAPHOS)
2,3-p-dioxandithiol-S,S-bis(O,O-diethyldithiophosphate) (DIOXATHION)
5-[(6-chloro-2-oxo-3-benzoxazolinyl)methyl]O,O-diethyldithiophosphate (PHOSALONE)
2-(diethoxyphosphinylimino)-1,3-dithiolane
O,O-dimethyl-S-[2-methoxy-1,3,4-thiadiazol-5-(4H)-onyl-(4)-methyl]dithiophosphate
O,O-dimethyl-S-phthalimidomethyl-dithiophosphate (IMIDAN)
O,O-diethyl-O-(3,5,6-trichloro-2-pyridyl)thiophosphate
O,O-diethyl-O-2-pyrazinylthiophosphate (THIONAZIN)
O,O-diethyl-O-(2-isopropyl-4-methyl-6-pyrimidyl)thiophosphate (DIAZINON)
O,O-diethyl-O-(2-quinoxalyl)thiophosphate O,O-dimethyl-S-(4-oxo-1,2,3-benzotriazin-3(4H)-ylmethyl)dithiophosphate (AZINPHOSMETHYL)
O,O-diethyl-S-(4-oxo-1,2,3-benzotriazin-3(4H)-ylmethyl)dithiophosphate (AZINPHOSETHYL)
S-[(4,6-diamino-s-triazin-2-yl)methyl]-O,O-dimethyldithiophosphate (MENAZON)
O,O-dimethyl-O-(3-chloro-4-nitrophenyl)thiophosphate (CHLORTHION)
O,O-dimethyl-O(or S)-2-(ethylthioethyl)thiophosphate (DEMETON-S-METHYL)
2-(O,O-dimethyl-phosphoryl-thiomethyl)-5-methoxypyrone-4-3,4-dichlorobenzyl-triphenylphosphoniumchloride
O,O-diethyl-S-(2,5-dichlorophenylthiomethyl)dithiophosphate (PHENKAPTON)
O,O-diethyl-O-(4-methyl-cumarinyl-7)-thiophosphate (POTASAN)
5-amino-bis(dimethylamido)phosphinyl-3-phenyl-1,2,4-triazole (TRIAMIPHOS)
N-methyl-5-(O,O-dimethylthiolphosphoryl)-3-thiavaleramide (VAMIDOTHION)
O,O-diethyl-O-[2-dimethylamino-4-methylpyrimidyl-(6)]-thiophosphate (DIOCTHYL)
O,O-dimethyl-S-(methylcarbamoylmethyl)-thiophosphate (OMETHOATE)
O-ethyl-O-(8-quinolinyl)-phenylthiophosphonate (OXINOTHIOPHOS)
O-methyl-S-methyl-amidothiophosphate (MONITOR)
O-methyl-O-(2,5-dichloro-4-bromophenyl)-benzothiophosphate (PHOSVEL)
O,O,O,O-tetrapropyldithiophosphate
3-(dimethoxyphosphinyloxy)-N-methyl-N-methoxy-cis-crotonamide
O,O-dimethyl-S-(N-ethylcarbamoylmethyl)dithiophosphate (ETHOATE-METHYL)
O,O-diethyl-S-(N-isopropylcarbamoylmethyl)-dithiophosphate (PROTHOATE)
S-N-(1-cyano-1-methylethyl)carbamoylmethyldiethylthiolphosphate (CYANTHOATE)
S-(2-acetamidoethyl)-O,O-dimethyldithiophosphate
Hexamethylphosphoric acid triamide (HEMPA)
O,O-dimethyl-O-(2-chloro-4-nitrophenyl)thiophosphate (DICAPTHON)
O,O-dimethyl-O-p-cyanophenyl thiophosphate (CYANOX)
O-ethyl-O-p-cyanophenylthiophosphonate
O,O-diethyl-O-2,4-dichlorophenylthiophosphate (DICHLORFENTHION)
O-2,4-dichlorophenyl-O-methylisopropylamidothiophosphate
O,O-diethyl-O-2,5-dichloro-4-bromophenylthiophosphate (BROMOPHOS-ETHYL)
dimethyl-p-(methylthio)phenylphosphate
O,O-dimethyl-O-p-sulphamidophenylthiophosphate
O-[p-(p-chlorophenyl)-azophenyl]O,O-dimethylthiophosphate (AZOTHOATE)
O-ethyl-S-4-chlorophenyl-ethyldithiophosphate
O-isobutyl-S-p-chlorophenyl-ethyldithiophosphate
O,O-dimethyl-S-p-chlorophenylthiophosphate
O,O-dimethyl-S-(p-chlorophenylthiomethyl)dithiophosphate
O,O-diethyl-p-chlorophenylmercaptomethyl-dithiophosphate (CARBOPHENOTHION)
O,O-diethyl-S-p-chlorophenylthiomethyl-thiophosphate
O,O-dimethyl-S-(carbethoxy-phenylmethyl)dithiophosphate (PHENTHOATE)
O,O-diethyl-S-(carbofluorethoxy-phenylmethyl)-dithiophosphate
O,O-dimethyl-S-carboisopropoxy-phenylmethyl)-dithiophosphate
O,O-diethyl-7-hydroxy-3,4-tetramethylene-coumarinyl-thiophosphate (COUMITHOATE)
2-methoxy-4-H-1,3,2-benzodioxaphosphorin-2-sulphide
O,O-diethyl-O-(5-phenyl-3-isooxazolyl)thiophosphate
2-(diethoxyphosphinylimino)-4-methyl-1,3-dithiolane
tris-(2-methyl-1-aziridinyl)-phosphine oxide (METEPA)
S-(2-chloro-1-phthalimidoethyl)-O,O-diethyldithiophosphate
N-hydroxynaphthalimido-diethylphosphate
dimethyl-3,5,6-trichloro-2-pyridylphosphate
O,O-dimethyl-O-(3,5,6-trichloro-2-pyridyl)thiophosphate
S-2-(ethylsulphonyl)ethyl dimethylthiolphosphate (DIOXYDEMETON-S-METHYL)
diethyl-S-2-(ethylsulphinyl)ethyl dithiophosphate (OXIDISULFOTON)
bis-O,O-diethylthiophosphoric acid anhydride (SULFOTEP)
dimethyl-1,3-di(carbomethoxy)-1-propen-2-yl-phosphate
dimethyl-(2,2,2-trichloro-1-butyroyloxyethyl)phosphate (BUTONATE)
O,O-dimethyl-O-(2,2-dichloro-1-methoxy-vinyl)phosphate
bis-(dimethylamido)fluorphosphate (DIMEFOX)
3,4-dichlorobenzyl-triphenylphosphoniumchloride
dimethyl-N-methoxymethylcarbamoylethyl-dithiophosphate (FORMOCARBAM)
O,O-diethyl-O-(2,2-dichloro-1-chloroethoxyvinyl)-phosphate
O,O-dimethyl-O-(2,2-dichloro-1-chloroethoxyvinyl)-phosphate
O-ethyl-S,S-diphenyldithiolphosphate
O-ethyl-S-benzyl-phenyldithiophosphonate
O,O-diethyl-S-benzyl-thiolphosphate
O,O-dimethyl-S-(4-chlorophenylthiomethyl)dithiophosphate (METHYLCARBOPHENOTHION)
O,O-dimethyl-S-(ethylthiomethyl)dithiophosphate
diisopropylaminofluorophosphate (MIPAFOX)
O,O-dimethyl-S-(morpholinylcarbamoylmethyl)dithiophosphate (MORPHOTHION)
bismethylamido-phenylphosphate
O,O-dimethyl-S-(benzenesulphonyl)dithiophosphate
O,O-dimethyl-(S and O)-ethylsulphinylethylthiophosphate
O,O-diethyl-O-4-nitrophenylphosphate
triethoxy-isopropoxy-bis(thiophosphinyl)disulphide
2-methoxy-4H-1,3,2-benzodioxaphosphorin-2-oxide
octamethylpyrophosphoramide (SCHRADAN)
bis-(dimethoxythiophosphinylsulphido)-phenylmethane
N,N,N',N'-tetramethyldiamidofluorophosphate (DIMEFOX)
O-phenyl-O-p-nitrophenyl-methanethiophosphonate (COLEP)
O-methyl-O-(2-chloro-4-tert.butyl-phenyl)-N-methylamidothiophosphate (NARLENE)
O-ethyl-O-(2,4-dichlorophenyl)-phenylthiophosphonate
O,O-diethyl-O-(4-methylmercapto-3,5-dimethylphenyl)-thiophosphate
4,4'-bis-(O,O-dimethylthiophosphoryloxy)-diphenyl disulphide O,O-di-(β-chloroethyl)-O-(3-chloro-4-methyl-coumarinyl-7)-phosphate
S-(1-phthalimidoethyl)-O,O-diethyldithiophosphate
O,O-dimethyl-O-(3-chloro-4-diethylsulphamylphenyl)-thiophosphate
O-methyl-O-(2-carbisopropoxyphenyl)-amidothiophosphate
5-(O,O-dimethylphosphoryl)-6-chloro-bicyclo(3.2.0)-heptadiene(1,5)
O-methyl-O-(2-i-propoxycarbonyl-1-methylvinyl)-ethylamidothiophosphate.

Nitrophenols and Derivatives 4,6-dinitro-6-methylphenol, sodium salt [Dinitrocresol]
dinitrobutylphenol-(2,2',2")-triethanolamine salt
2-cyclohexyl-4,6-dinitrophenyl [Dinex]
2-1-methylheptyl)-4,6-dinitrophenyl-crotonate [Dinocap]
2-sec.butyl-4,6-dinitrophenyl-3-methyl-butenoate [Binapacryl]
2-sec.butyl-4,6-dinitrophenyl-cyclopropionate
2-sec.butyl-4,6-dinitrophenylisopropylcarbonate [Dinobuton]

Miscellaneous pyrethrin I
pyrethrin II
3-allyl-2-methyl-4-oxo-2-cyclopentan-1-yl-chrysanthemumate (Allethrin)
6-chloropiperonyl-chrysanthemumate (Barthrin)
2,4-dimethylbenzyl-chrysanthemumate (Dimethrin)
2,3,4,5-tetrahydrophthalimidomethylchrysanthemumate
4-chlorobenzyl-4-chlorophenylsulphide [Chlorobensid]
6-methyl-2-oxo-1,3-dithiolo-[4,5-b]-quinoxaline (Quinomethionate)
(I)-3-(2-furfuryl)-2-methyl-4-oxocyclopent-2-enyl(I)-(cis+trans)-chrysanthemum-monocarboxylate [Furethrin]
2-pivaloyl-indane-1,3-dione [Pindon]
4-chlorobenzyl-4-fluorophenyl-sulphide [Fluorobenside]
5,6-dichloro-1-phenoxycarbamyl-2-trifluoromethyl-benzimidazole [Fenozaflor]
p-chlorophenyl-p-chlorobenzenesulphonate [Ovex]
p-chlorophenyl-benzenesulphonate [Fenson]
p-chlorophenyl-2,4,5-trichlorophenylsulphone [Tetradifon]
p-chlorophenyl-2,4,5-trichlorophenylsulphide [Tetrasul]
p-chlorobenzyl-p-chlorophenylsulphide [Chlorobenside]
2-thio-1,3-dithiolo-(5,6)-quinoxaline [Thiochinox]
prop-2-ynyl-(4-t-butylphenoxy)-cyclohexylsulphite [Propargil].

Formamidines 1-dimethyl-2-(2'-methyl-4'-chlorophenyl)-formamidine (CHLORPHENAMIDIN)
1-methyl-2-(2'-methyl-4'-chlorophenyl)-formamidine
1-methyl-2-(2'-methyl-4'-bromophenyl)-formamidine
1-methyl-2-(2',4'-dimethylphenyl)-formamidine
1-n-butyl-1-methyl-2-(2'-methyl-4'-chlorophenyl)-formamidine
1-methyl-1-(2'-methyl-4'-chloroaniline-methylene)-formamidine
2-(2"-methyl-4"-chlorophenyl-formamidine
1-n-butyl-2-(2'-methyl-4'-chlorophenyl-imino)-pyrolidine.

Urea

N-2-methyl-4-chlorophenyl-N',N'-dimethyl-thiourea.

Carbamates 1-naphthyl-N-methylcarbamate (CARBARYL)
2-butinyl-4-chlorophenylcarbamate
4-dimethylamino-3,5-xylyl-N-methylcarbamate
4-dimethylamino-3-tolyl-N-methylcarbamate (AMINOCARB)
4-methylthio-3,5-xylyl-N-methylcarbamate (METHIOCARB)
3,4,5-trimethylphenyl-N-methylcarbamate
2-chlorophenyl-N-methylcarbamate (CPMC)
5-chloro-6-oxo-2-norborane-carbonitrile-O-(methylcarbamoyl)-oxime
1-(dimethylcarbamoyl-5-methyl-3-pyrazolyl)-N,N-dimethylcarbamate (DIMETILAN)
2,3-dihydro-2,2-dimethyl-7-benzofuranyl-N-methylcarbamate (CARBOFURAN)
2-methyl-2-methylthio-propionaldehyde-O-(methylcarbamoyl)oxime (ALDICARB)
8-quinaldyl-N-methylcarbamate and its salts
methyl-2-isopropyl-4-(methylcarbamoyloxy)carbanilate
m-(1-ethylpropyl)phenyl-N-methylcarbamate
3,5-di-tert.butyl-N-methylcarbamate
m-(1-methylbutyl)phenyl-N-methylcarbamate
2-isopropylphenyl-N-methylcarbamate
2-sec.butylphenyl-N-methylcarbamate
m-tolyl-N-methylcarbamate
2,3-xylyl-N-methylcarbamate
3-isopropylphenyl-N-methylcarbamate
3-tert.butylphenyl-N-methylcarbamate
3-sec.butylphenyl-N-methylcarbamate
3-isopropyl-5-methylphenyl-N-methylcarbamate (PROMECARB)
3,5-diisopropylphenyl-N-methylcarbamate
2-chloro-5-isopropylphenyl-N-methylcarbamate
2-chloro-4,5-dimethylphenyl-N-methylcarbamate
2-(1,3-dioxolan-2-yl)phenyl-N-methylcarbamate (DIOXACARB)
2-(4,5-dimethyl-1,3-dioxolan-2-yl)-phenyl-N-methylcarbamate
2-(1,3-dioxolan-2-yl)phenyl-N,N-dimethylcarbamate
2-(1,3-dithiolan-2-yl)-N,N-dimethylcarbamate
2-(1,3-dithiolan-2-yl)phenyl-N,N-dimethylcarbamate
2-isopropoxyphenyl-N-methylcarbamate (APROCARB)
2-(2-propinyloxy)phenyl-N-methylcarbamate
3-(2-propinyloxy)phenyl-N-methylcarbamate
2-dimethylaminophenyl-N-methylcarbamate
2-diallylaminophenyl-N-methylcarbamate
4-diallylamino-3,5-xylyl-N-methylcarbamate (ALLYXICARB)
4-benzothienyl-N-methylcarbamate
2,3-dihydro-2-methyl-7-benzofuranyl-N-methylcarbamate
3-methyl-1-phenylpyrazol-5-yl-N,N-dimethylcarbamate
1-isopropyl-3-methylpyrazol-5-yl-N,N-dimethylcarbamate (ISOLAN)
2-dimethylamino-5,6-dimethylpyrimidin-4-yl-N,N-dimethylcarbamate
3-methyl-4-dimethylaminomethyleneiminophenyl-N-methylcarbamate 3,4-dimethylphenyl-N-methylcarbamate
2-cyclopentylphenyl-N-methylcarbamate
3-dimethylamino-methyleneiminophenyl-N-methylcarbamate (FORMETANATE) and its salts
1-methylthio-ethylimino-N-methylcarbamate (METHOMYL)
2-methylcarbamoyloximino-1,3-dithiolane
5-methyl-2-methylcarbamoyloximino-1,3-oxythiolane
2-(1-methoxy-2-propoxy)phenyl-N-methylcarbamate
2-(1-butin-3-yl-oxy)phenyl-N-methylcarbamate
1-dimethylcarbamyl-1-methylthio-O-methylcarbamyl-formoxime
1-(2'-cyanoethylthio)-O-methylcarbamyl-acetaldoxime
1-methylthio-O-carbamyl-acetaldoxime
O-(3-sec.butylphenyl)-N-phenylthio-N-methylcarbamate
2,5-dimethyl-1,3-dithiolane-2-(O-methylcarbamyl)-aldoxime)
O-2-diphenyl-N-methylcarbamate
2-(N-methylcarbamyl-oximino)-3-chloro-bicyclo[2.2.1]heptane
2-(N-methylcarbamyl-oximino)-bicyclo[2.2.1]heptane
3-isopropylphenyl-N-methyl-N-chloroacetal-carbamate
3-isopropylphenyl-N-methyl-N-methylthiomethyl-carbamate
O-(2,2-dimethyl-4-chloro-2,3-dihydro-7-benzofuranyl)-N-methyl-carbamate
O-(2,2,4-trimethyl-2,3-dihydro-7-benzofuranyl)-N-methylcarbamate
O-naphthyl-N-methyl-N-acetal-carbamate
O-5,6,7,8-tetrahydronaphthyl-N-methyl-carbamate
3-isopropyl-4-methylthio-phenyl-N-methylcarbamate
3,5-dimethyl-4-methoxy-phenyl-N-methylcarbamate
3-methoxymethoxy-phenyl-N-methylcarbamate
3-allyloxyphenyl-N-methylcarbamate
2-propargyloxymethoxy-phenyl-N-methyl-carbamate
2-allyloxyphenyl-N-methyl-carbamate
4-methoxycarbonylamino-3-isopropylphenyl-N-methyl-carbamate
3,5-dimethyl-4-methoxycarbonylamino-phenyl-N-methyl-carbamate
2-γ-methylthiopropylphenyl-N-methyl-carbamate
3-(α-methoxymethyl-2-propenyl)-phenyl-N-methyl-carbamate
2-chloro-5-tert.-butyl-phenyl-N-methyl-carbamate
4-(methyl-propargylamno-3,5-xylyl-N-methyl-carbamate
4-(methyl-γ-chloroallylamio)-3,5-xylyl-N-methyl-carbamate
4-(methyl-β-chloroallylamino)-3,5-xylyl-N-methyl-carbamate
1-(β-ethoxycarbonylethyl)-3-methyl-5-pyrazolyl-N,N-dimethylcarbamate
3-methyl-4-(dimethylamino-methylmercapto-methyleneimino)-phenyl-N-methyl-carbamate
1,3-bis(carbamoylthio)-2-(N,N-dimethylamino)-propanehydrochloride
5,5-dimethylhydroresorcinoldimethylcarbamate
2-[ethyl-propargylamino]-phenyl-N-methylcarbamate
2-[methyl-propargylamino]-phenyl-N-methylcarbamate
4-[dipropargylamino]-3-tolyl-N-methylcarbamate
4-[dipropargylamino]-3,5-xylyl-N-methylcarbamate
2-[allyl-isopropylamino]-phenyl-N-methylcarbamate
3-[allyl-isopropylamino]-phenyl-N-methylcarbamate Chlorinated Hydrocarbons γ-hexachlorocyclohexane [GAMMEXANE; LINDAN; γ HCH]

1,2,4,5,6,7,8,8-octachloro-3α,4,7,7α-tetrahydro-4,7-methylene indane [CHLORDAN]
1,4,5,6,7,8,8-heptachloro-3α,4,7,7α-tetrahydro-4,7-methylene indane [HEPTACHLOR]
1,2,3,4,10,10-hexachloro-1,4,4α,5,8,8α-hexahydro-endo-1,4-exo-5,8-dimethanonaphthalene [ALDRIN]
1,2,3,4,10,10-hexachloro-6,7-epoxy-1,4,4α,5,6,7,8,8α-octahydro-exo-1,4-endo-5,8-dimethanonaphthalene [DIFLORIN]
1,2,3,4,10,10-hexachloro-5,7-epoxy-1,4,4α,5,6,7,8,8α-octahydro-endo-endo-5,8-dimethanonaphthalene [ENDRIN]

The compounds of the formula I may be used as pure active substance or together with suitable carriers and/or additives. Suitable carriers and additives can be solid or liquid and correspond to the substances conventionally used in formulation technique such, for example, as solvents, dispersants, wetting agents, adhesives, thickeners, binders and/or fertilisers.

For application, the compounds of the formula I may be processed to dusts, emulsion concentrates, granules, dispersions, sprays, to solutions, or suspensions, in the conventional formulation which is commonly employed in application technology. Mention may also be made of cattle dips and spray races, in which aqueous preparations are used.

The agents according to the invention are manufactured in known manner by intimately mixing and/or grinding active substances of the formula I with the suitable carriers, optionally with the addition of dispersants or solvents which are inert towards the active substances. The active substances may take, and be used in, the following forms:

Solid forms:
  Dusts, tracking agents, granules, coated granules, impregnated granules and homogeneous granules.
Liquid forms:
  (a) active substances which are dispersible in water: wettable powders, pasts, emulsions;
  (b) solutions.

To manufacture solid forms (dusts, tracking agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used singly or in admixture with one another.

Granules can be very easily manufactured by dissolving an active substance of the formula I in an organc solvent and applying the resulting solution to a granulated material, for example attapulgite, $SIO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mold polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added addtives which stabilise the active substance and/or non-ionic, anionic and cationic surface active substances, which, for example, improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilise the active substance, surface-active substance and anti-foam agents and, optionally, solvents.

Wettable powders and pastes are obtained by mixing and grinding the active substances with dispersing agents and pulverulent carriers in suitable apparatus until homogeneity is attained. Suitable carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl ethionate, the sodium salts of oleoyl methyl tauride, ditertiary acetylene glycols, dialkyl dilauryl ammonium chloride and fatty acid alkali and alkaline earth metal salts.

Suitable anti-foam agents are silicones.

The active substances are mixed, ground, sieved and strained with the additives cited hereinabove, in such a manner that, the size of the solid particles does not exceed 0.02 to 0.04μ in wettable powders, and 0.03μ in pastes. To produce emulsifiable concentrates and pastes, dispersing agents such as those cited above, organic solvents, and water are used. Examples of suitable solvents are: alcohols, benzene, xylene, toluene, dimethyl sulphoxide, and mineral oil fractions which boil between 120° and 350° C. The solvents must be practically odourless, not phytotoxic, and inert to the active substances.

Furthermore, the agents according to the invention can be applied in the form of solutions. For this purpose the active substances, or several active substances of the general formula I, are dissolved in suitable organic solvents, mixtures of solvents or in water. Aliphatic and aromatic hydrocarbons, chlorinated derivatives thereof, alkyl naphthalenes, and mineral oils, singly or in admixture with each other, can be used as organic solvents.

The content of active substance in the above described agents is between 0.1% to 95%, in which connection it should be mentioned that, in the case of application from aircraft or some other suitable means of application, it is possible to use concentrations of up to 99.5% or even pure active substance.

The active substances of the formula I can, for example, be formulated as follows:

Dusts

The following substances are used to manufacture (a) a 5% and (b) a 2% dust:

(a)

5 parts of active substance
95 parts of talcum (b)

2 part of active substance
1 part of highly disperse silicic acid
97 parts of talcum.

The active substances are mixed with the carriers and ground.

Granules

The following substances are used to produce 5% granules:

5 parts of active substance,
0.25 parts of epichlorohydrin,
0.25 parts of cetyl polyglycol ether,
3.50 parts of polyethylene glycol,
91 parts of kaolin (particle size 0.3–0.8 mm).

The active substance is mixed with epichlorohydrin and dissolved with 6 parts of acetone; the polyethylene glycol and cetyl polyglycol ether are then added. The thus obtained solution is sprayed on kaolin, and the acetone subsequently evaporated in vacuo.

Wettable powder

The following constituents are used for the preparation of (a) a 40%, (b) and (c) a 25%, and (d) a 10% wettable powder:

(a)

40 parts of active substance,
5 parts of sodium lignin sulphonate,
1 part of sodium dibutyl-naphthalene sulphonate,
54 parts of silicic acid.

(b)

25 parts of active substance,
4.5 parts of calcium lignin sulphonate,
1.9 parts of Champagne chalk/hydroxyethyl cellulose mixture (1:1), 1.5 parts of sodium dibutyl naphthalene sulphonate,
19.5 parts of silicic acid,
19.5 parts of Champagne chalk,
28.1 parts of kaolin.

(c)

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminum silicate,
16.5 parts of kieselguhr,
46 parts of kaolin.

(d)

10 parts of active substance,
3 of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates

The following substances are used to produce a) a 10% and b) a 25% emulsifiable concentrate:

(a)

10 parts of active substance,
3.4 parts of epoxidised vegetable oil,
13.4 parts of a combination emulsifier consisting of fatty alcohol polyglycol ether and alkylarylsulphonate calcium salt,
40 parts of dimethylformamide,
43.2 parts of xylene.

(b)

25 parts of active substance,
2.5 parts of epoxidised vegetable oil,
10 parts of an alkylarylsulphonate/fatty alcoholpolyglycol ether mixture,
5 parts of dimethylformamide,
57.5 parts of xylene.

From these concentrates it is possible to produce, by dilution with water, emulsions of any desired concentration.

Spray

The following constituents are used to prepare a 5% spray:

5 parts of active substance,
1 part of epichlorohydrin,
94 parts of benzine (boiling limits 160°–190° C.).

The following Examples will serve to illustrate the manufacture of the compounds of the formula I.

EXAMPLE 1

To a solution of 19.8 g of 4-hydroxy-diphenyl ether in 80 ml of acetone were added 16.5 g of anhydrous pulverised potassium carbonate and then, while stirring, 20.8 g of 3-methyl-4-bromo-2-butenoic acid ethyl ester (mixture of 80% trans- and 20% of cis-compound) were added dropwise within one hour at the boiling temperature of the mixture. Stirring was continued for 8 hours at reflux temperature after addition of the bromide. The reaction mixture was processed by filtering of the acetone solution from the precipitate with suction, washing the residue with acetone, and removing the acetone in vacuo. The residue was taken up in 20 ml of ether/hexane (1:5) and this solution was washed firstly 4 times with 50 ml of 5% ice-cold, aqueous potassium hydroxide solution, and subsequently 4 times with water. The organic phase was dried over sodium sulphate and the solvent and readily volatile constituents were completely removed in vacuo, to leave as residue pure 4-[4-(phenoxy)-phenoxy]-3-methyl-2-butenoic acid ethyl ester (cis/trans). $n_D^{20} = 1.5598$.

EXAMPLE 2

To a solution of 18.6 g of 4-amino-diphenyl ether in 100 ml of 1,2-dimethoxy ethane were added 15.6 g of ethyl diisopropylamine and then, while stirring, a solution of 19.3 g of 3-methyl-4-bromo-2-trans-butenoic acid methyl ester in 80 ml of 1,2-dimethoxy ethane was added at room temperature within 8 hours. Stirring was then continued for 20 hours at room temperature. The reaction mixture was processed by filtering of precipitated ethyl diisopropylammonium bromide, washing with ether and freeing the filtrate from solvent in vacuo. The resulting crude product was further purified by chromatography on silica gel (eluant: ether/hexane 1:2) to yield pure 4-[4-(phenoxy)-anilino]-3-methyl-2-trans-butenoic acid methyl ester. $n_D^{20} = 1.5891$.

EXAMPLE 3

While stirring, a solution of 6 g of 4-[4-(phenoxy)anilino]-3-methyl-2-trans-butenoic acid methyl ester in 5 ml of anhydrous formic acid was added dropwise at 0° C. and within about 30 minutes to 12 ml of a mixture of 102 parts of acetic anhydride and 92 parts of anhydrous formic acid (which mixture had been heated for 1 hour to 45° C. before the formation of the mixed acetic acid/formic acid anhydride). The reaction mixture was subsequently kept at 0° to 5° C. for 6 hours and at 30° C. for a further 24 hours. The reaction mixture was then treated with 50 ml of water while gently cooling with ice and stirred for 1 hour at 10°–15° C. The reaction mixture was then repeatedly extracted with ether and the combined ether phases were washed neutral first with saturated sodium hydrogen carbonate solution and subsequently with water. After ethereal solution had been dried over sodium sulphate and the solvent completely removed in vacuo, the residual 4-[4-(phenoxy)-N-formylanilino]-3-methyl-2-trans-butenoic acid methyl ester was further purified by chromatography on silica gel. Melting point: 93°–95° C.

EXAMPLE 4

3 g of about 50% sodium hydride in mineral oil was washed repeatedly with hexane and put into a sulphurating flask in 80 ml of absolute tetrahydrofuran. While stirring, 16.6 g of diethylphosphonoacetic acid diethylamide in 20 ml of absolute tetrahydrofuran were added dropwise at 0°–5° C. within about 45 minutes. The mixture was heated to room temperature and stirring continued for 30 minutes. It was then cooled again to 5° C. and, while stirring, a solution of 14.4 g of 1-[4-(benzyl)phenoxy]-propan-2-one in 40 ml of absolute tetrahydrofuran was added dropwise within 1 hour. After 2 hours the reaction mixture was heated to 30° C. and kept for 2 hours at this temperature. The reaction mixture was processed by distilling off the bulk of the tetrahydrofuran in vacuo, partitioning the residue between water and diethyl ether, and repeatedly washing the aqueous phase with ether. The combined ethereal phases were dried over sodium sulphate and the solvent was distilled off. The residue was further purified on silica gel by chromatography (eluant: methyl acetate/-diethyl ether/hexane 1:4:2) to yield pure 4-[4-(benzyl)-phenoxy]-3-methyl-2-cis/transbutenoic acid diethyl amide. $n_D^{20} = 1.5596$.

In the same way, e.g. by reacting 1-[4-(benzyl)-phenoxy]-propan-2-one with diethylphosphonoacetic acid isopropyl ester and subsequent chromatography on silica gel, 4-[4-benzyl)-phenoxy]-3-methyl-2-transbutenoic acid isopropyl ester ($n_D^{20} = 1.5512$) and 4-[4-(benzyl)-phenoxy]-3-methyl-2-cisbutenoic acid isopropyl ester ($n_D^{20} = 1.5451$) were obtained.

The 1-[4-(benzyl)-phenoxy]-propan-2-one used as starting product was manufactured as follows:

While stirring, a previously prepared mixture of 22.3 g of mercury oxide, 0.8 g of trichloroacetic, 8 ml of boron trifluoride diethyl etherate and 20 ml of absolute methanol was added all at once to a solution, cooled to −5° C., of 11.1 g of 4-benzylpropargyloxybenzene ($n_D^{20} = 1.5807$) in 400 ml of absolute methanol. After about 10 minutes the external cooling was reduced so that the temperature of the reaction mixture (exothermic reaction) was slowly able to rise to a maximum of 45° C. The external cooling was again intensified at this temperature and the reaction mixture kept for a further 3 hours at about 20°-25° C. During the course of the reaction the colour of the mixture turned from orange to pale grey. The diethyl ketal formed was isolated by pouring the contents of the flask, cooled to about 0° C., on the mixture of 125 ml of 2 normal sodium carbonate solution and 500 g of ice. After stirring for about 10 minutes the whole mixture was acidified with 750 ml of 2 normal phosphoric acid and treated with 700 ml of diethyl ether. The batch was filtered through a layer of diatomaceous earth, the ether phase isolated, and the aqueous phase extracted 3 times with diethyl ether. The combined ethereal phases were washed with 200 ml of 5% ice-cold potassium hydroxide solution and 3 times with 300 ml of saturated sodium chloride solution. The organic phase was dried over sodium sulphate and the solvent then completely distilled off. The resulting 1-[4-(benzyl)phenoxy]-propan-2-on-dimethyl ketal was immediately dissolved in a mixture of 600 ml of acetone, 100 ml of water, and 35 ml of normal hydrochloric acid and hydrolysed to the ketone by being left to stand for 5 hours at room temperature. The ketone was isolated by pouring the reaction mixture into 600 ml of saturated sodium chloride solution, isolating the organic phase, and washing the aqueous phase 3 times with diethyl ether. The combined organic phases were washed finally 3 times with saturated sodium chloride solution, dried over sodium sulphate, and the solvent was completely removed in vacuo. The crude ketone, which congeals at once in crystalline form, was recrystallised from isopropanol to yield pure 1-[4-(benzyl)-phenoxy]-propan-2-one which melts at 51°-52° C.

In wholly analogous manner it is possible to manufacture from 4-propargyloxy-diphenyl ether ($n_D^{20} = 1.5825$), 4-propargyloxybenzophenone (m.p. 72°-73° C.) and 2-[4-(phenoxy)phenoxy]-3-butine (m.p. 53°-54° C.) the following ketones which are used as intermediates: 1-[4-(phenoxy)-phenoxy]propan-2-one (m.p. 47°-48° C.), 1-[4-(benzoyl)-phenoxy]propan-2-one (m.p. 51°-52° C.), and 2-[4-(phenoxy)-phenoxy]butan-3-one (m.p. 36°-37° C.).

The following compounds are also manufactured in analogous manner as described in Example 1 to 4:

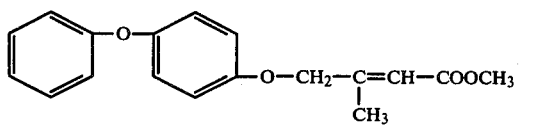

m.p.: 55°-56° C.

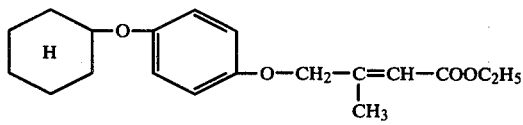

m.p.: 46°-48° C.

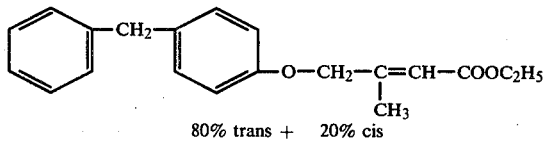

80% trans + 20% cis $n_D^{20}$ : 1,5560

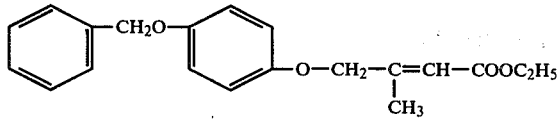

m.p.: 74°-76° C.

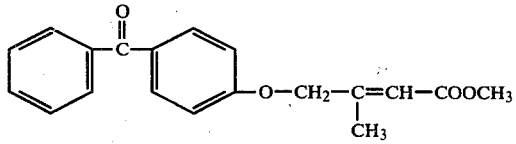

m.p.: 105°-107° C.

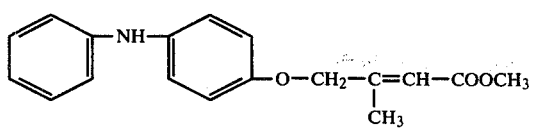

m.p.: 65°-67° C.

-continued
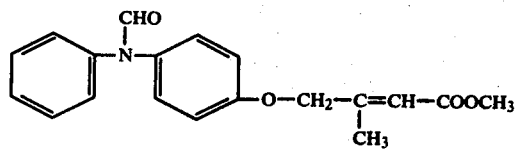
m.p.: 101°-102° C.
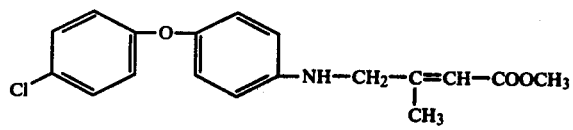
$n_D^{20}$ : 1,5955
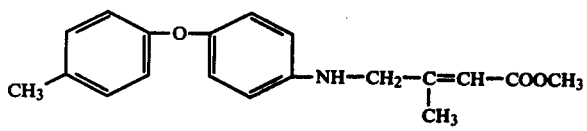
m.p.: 68°-69° C.
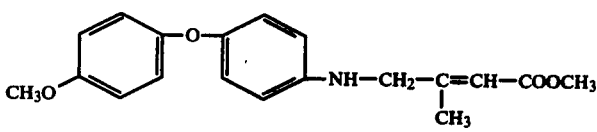
$n_D^{20}$ : 1,5884
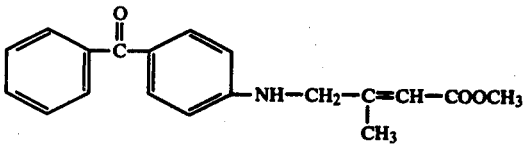
m.p.: 100°-102° C.
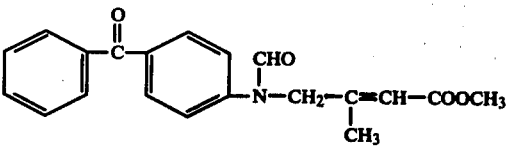
m.p.: 110°-112° C.
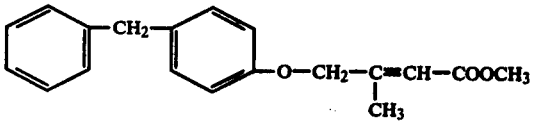
$n_D^{20}$ : 1,5553
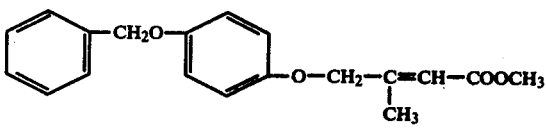
$n_D^{20}$ : 1,5624
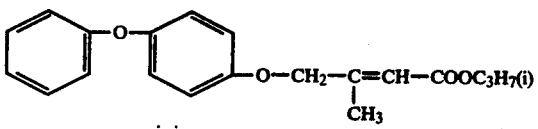
cis-isomere
$n_D^{20}$ : 1,5470
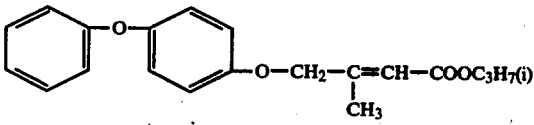
trans-isomere
$n_D^{20}$ : 1,5522
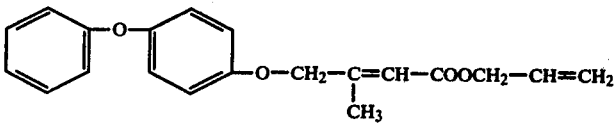
$n_D^{20}$ : 1,5571
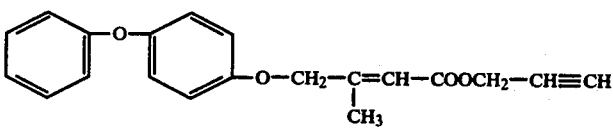
$n_D^{20}$ : 1,5640

-continued
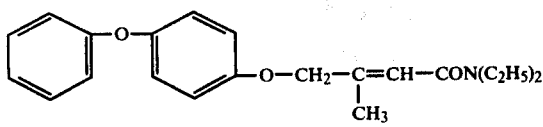
$n_D^{20}$ : 1,5610
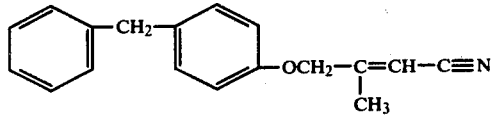
$n_D^{20}$ : 1,5732
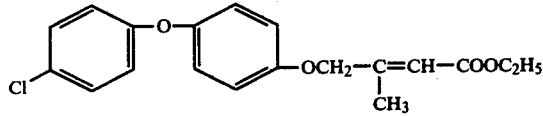
m.p.: 45°–47° C.
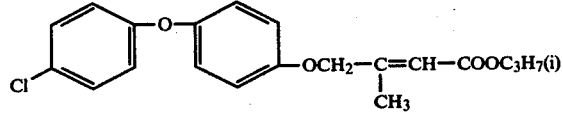
m.p.: 49°–50° C.
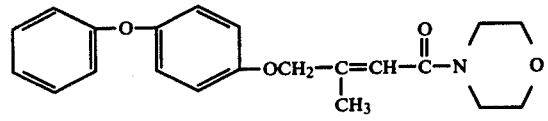
m.p.: 69°–70° C.
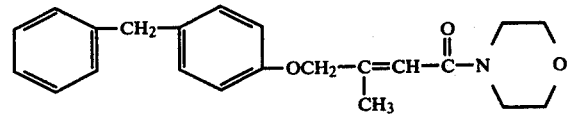
m.p.: 80°–81° C.
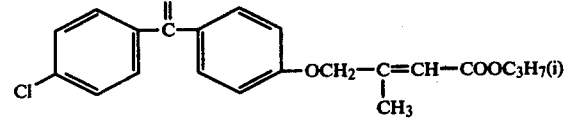
m.p.: 85°–87° C.
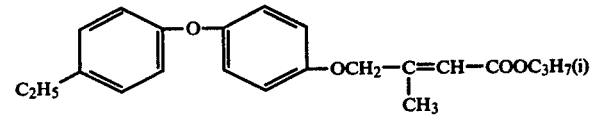
$n_D^{20} = 1,546$
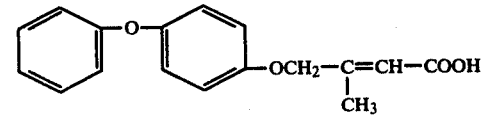
m.p.: 117°–119° C.
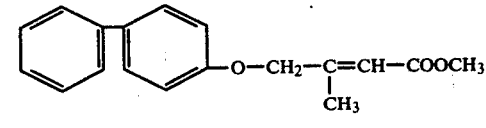
$n_D^{20} = 1,5888$
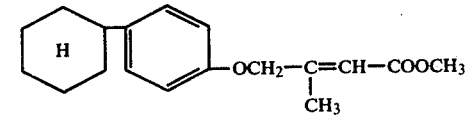
$n_D^{20} = 1,5294$
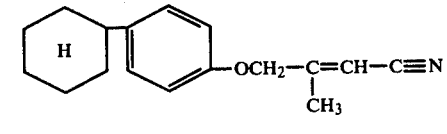
m.p.: 59°–62° C.
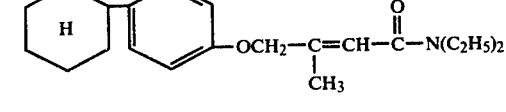
$n_D^{20} = 1,5328$ -continued
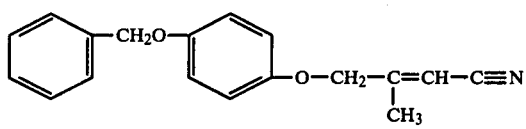 m.p.: 102°-104° C.
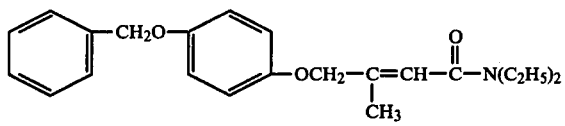 m.p.: 64°-66° C.
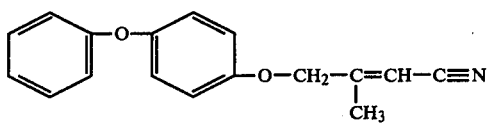 $n_D^{20}$ = 1.5732
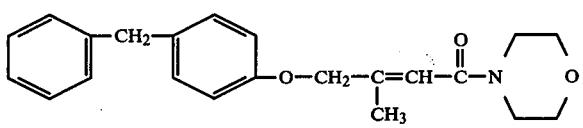 $n_D^{20}$ = 1.5815
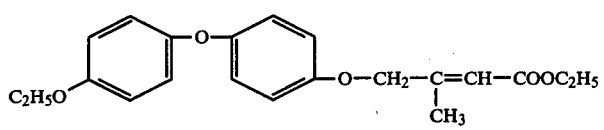 m.p.: 63°-65° C.
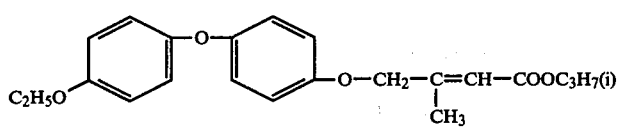 m.p.: 56°-57° C.
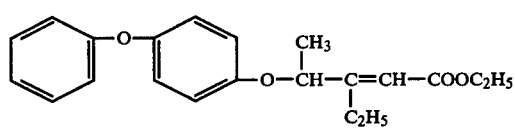 m.p.: 45°-47° C.
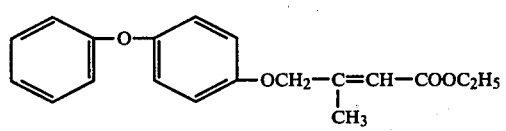 $n_D^{20}$ = 1.5428
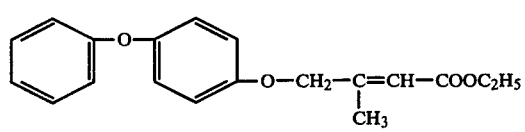 $n_D^{20}$ = 1.5623
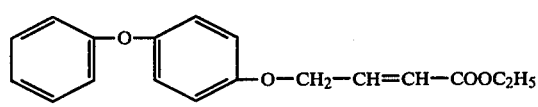 m.p.: 65°-66° C.
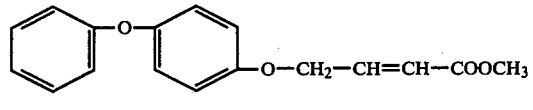 m.p.: 73°-75° C.
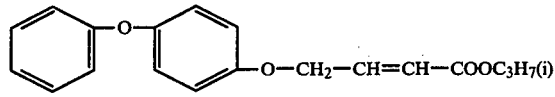
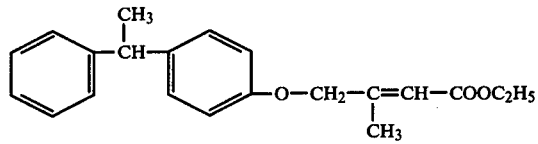

-continued
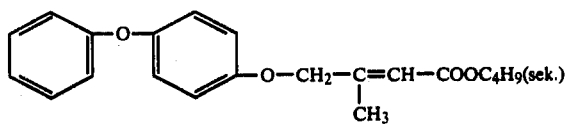 $n_D^{20} = 1{,}5480$
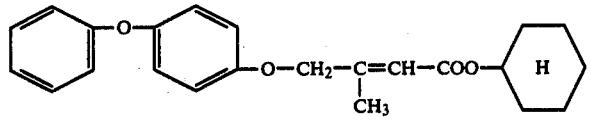 $n_D^{20} = 1{,}5588$
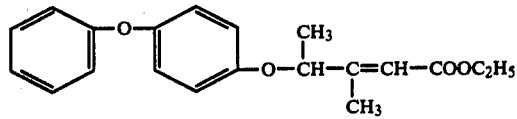 $n_D^{20} = 1{,}5535$
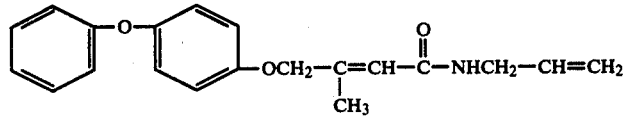 m.p.: 86°–87° C.
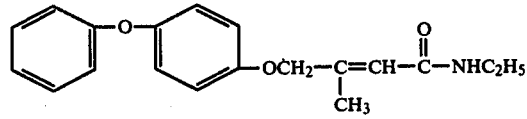 m.p.: 95°–96° C.
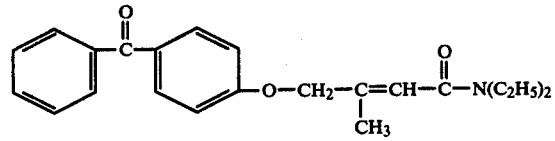 m.p.: 78°–80° C.
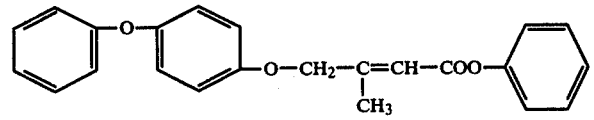
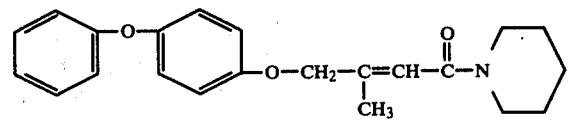
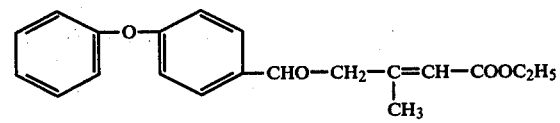
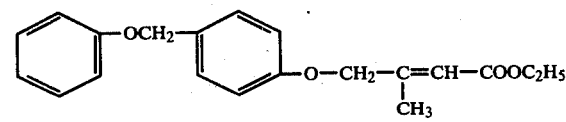
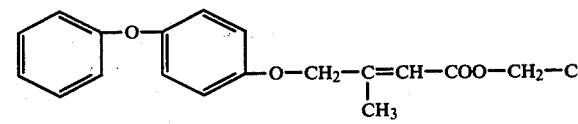
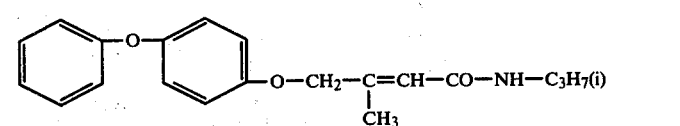
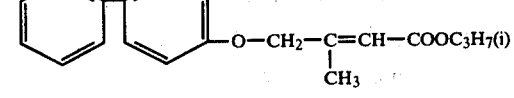

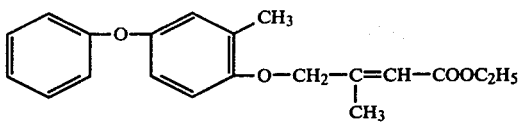

EXAMPLE 5

(A) Topical action on *Dysdercus fasciatus* larvae

10 Dysdercus fasciatus larvae were treated topically with solutions of active substance in acetone 8–10 days before they were due to shed and emerge to the adult stage. The larvae were then kept at 28° C. and 80–90% relative humidity. They were fed with meal made from premoistened cotton seeds. After about 10 days, i.e. as soon as the untreated larvae had shed, the test subjects were examined for the number of normal adults.

(B) Contact action on Dysdercus fasciatus larvae

A specific amount of a 0.1% solution of active substance in acetone (corresponding to 10 mg/of active substance/m$^2$) was pipetted into an aluminium dish and evenly distributed.

After the acetone had evaporated, 10 larvae of the 5th. stage of *Dysdercus fasciatus* were put into the treated dish which contained feed and moist cotton wool. The dish was then covered with a sieve cover. After about 10 days, i.e. as soon as the control larvae had shed and emerged to the adult stage, the test subjects were examined for the number of normal larvae. In the above tests A and B the compounds according to Examples 1 to 4 displayed good action.

EXAMPLE 6

Topical action of *Dermestes lardarius* pupae 10 fresh pupae of *Dermestes lardarius* were treated topically with solutions of active substance in acetone. The pupae were then kept at 28° C. and 80–90% relative humidity. After about 10 days, i.e. as soon as the controls had left their cocoons as Imagines, the test subjects were examined for the number of normal adults. In the above test the compounds according to Examples 1 to 4 displayed good action.

EXAMPLE 7

Contact action on *Aëdes aegypti* larvae

About 20 two day old larvae of the yellow fly (*Aëdes aegypti*) were put into a beaker containing a solution of the active substance (concentration 5 ppm). The beaker was then covered with a sieve cover. After the controls had shed and emerged to the adult stage, the test subjects were examined and the percentage number of normal adults ascertained in comparison to the control.

In the above test the compounds according to Examples 1 to 4 displayed good action.

EXAMPLE 8

Contact action on *Tenebrio molitor* pupae

A specific amount of a solution of active substance in acetone (corresponding to 10 mg of active substance/m$^2$) was pipetted into an aluminium dish and evenly distributed.

After the acetone had evaporated, 10 freshly shed pupae were laid on the treated surface. The dish was covered with a sieve cover.

After the controls had left their cocoons as Imagines the test subjects were examined for the number of normal adults.

In the above test the compounds according to Examples 1 to 4 displayed good action.

I claim:

1. A compound of the formula

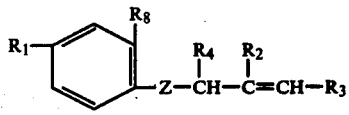

wherein
$R_1$ represents the group

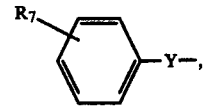

in which
Y represents

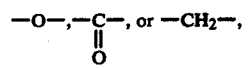

$Z$ represents —O—,
$R_2$ represents methyl or ethyl,
$R_3$ represents methoxycarbonyl, ethoxycarbonyl, isopropoxycarbonyl, sec. butoxycarbonyl, or cyclohexyloxycarbonyl,
$R_4$ represents hydrogen, and
$R_7$ represents hydrogen, methyl, ethyl, chlorine, methoxy or ethoxy.

2. The compound according to claim 1, wherein $R_1$ represents the group

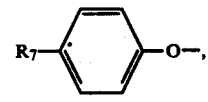

$Z$ represents —O—, $R_2$ represents methyl or ethyl, $R_3$ represents methoxycarbonyl, ethoxycarbonyl, isopropoxycarbonyl, or sec. butoxycarbonyl, $R_4$ represents hydrogen, and $R_7$ represents hydrogen, chlorine or ethyl.

3. The compound according to claim 1, wherein $R_1$ represents unsubstituted benzyl, Z represents —O—, $R_2$ represents methyl, $R_3$ represents methoxycarbonyl, ethoxycarbonyl, or isopropoxycarbonyl, and $R_7$ represents hydrogen.

4. 4-[4-(phenoxy)-phenoxy]-3-methyl-2-butenoic acid methyl ester according to claim 2.

5. 4-[4-(phenoxy)-phenoxy]-3-methyl-2-butenoic acid ethylester according to claim 2.

6. 4-{4-[4-(chloro)-phenoxy]-phenoxy}-3-methyl-2-butenoic acid ethyl ester according to claim 2.

7. 4-{4-[4-(chloro)-phenoxy]-phenoxy}-3-methyl-2-butenoic acid isopropyl ester according to claim 2.

8. 4-[4-(benzyl)-phenoxy]-3-methyl-2-butenoic acid isopropyl ester according to claim 3.

9. 4-{4-[4-(ethyl)-phenoxy]-phenoxy}-3-methyl-2-butenoic acid isopropyl ester according to claim 2.

10. 4-[4-(benzyl)-phenoxy]-3-methyl-2-butenoic acid ethyl ester according to claim 3.

11. 4-[4-(benzyl)-phenoxy]-3-methyl-2-butenoic acid methyl ester according to claim 3.

12. 4-[4-(benzoyl)-phenoxy]-3-methyl-2-butenoic acid methyl ester according to claim 1.

13. 4-[4-(phenoxy)-phenoxy]-3-methyl-2-butenoic acid sec. butyl ester according to claim 2.

14. 4-[4-(phenoxy)-phenoxy]-3-methyl-2-butenoic acid isopropyl ester according to claim 2.

15. 4-[4-(phenoxy)-phenoxy]-3-methyl-2-butenoic acid allyl ester.

16. 4-[4-(phenoxy)-phenoxy]-3-methyl-2-butenoic acid propargyl ester.

17. 4-[4-(phenoxy)-phenoxy]-3-methyl-2-butenoic acid 3-chloroallyl ester.

18. An insecticidal composition comprising an insecticidally effective amount of a compound according to claim 1 together with a suitable carrier therefor.

19. A method for combatting insects which comprises applying to the locus thereof an insecticidally effective amount of a compound according to claim 1.

* * * * *